(12) United States Patent
O'Dwyer et al.

(10) Patent No.: US 6,204,019 B1
(45) Date of Patent: Mar. 20, 2001

(54) **SEC A2 FROM *STREPTOCOCCUS PNEUMONIAE***

(75) Inventors: Karen M O'Dwyer, Phoenixville; Richard Warren, Blue Bell; Caroline Perry, Chester Springs, all of PA (US)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 08/868,699

(22) Filed: Jun. 4, 1997

(51) Int. Cl.[7] ............................. C12N 15/09; C12N 1/20; C07H 21/04

(52) U.S. Cl. .................... 435/69.3; 435/70.1; 435/71.1; 435/71.2; 435/252.3; 435/254.11; 435/320.1; 435/325; 536/23.7; 935/12; 935/22; 935/66

(58) Field of Search .................... 435/69.1, 70.1, 435/71.1, 71.2, 325, 252.3, 254.11, 320.1, 883; 536/23.2, 23.7, 24.3, 24.32; 935/12, 22, 66

(56) References Cited

U.S. PATENT DOCUMENTS 5,175,101 * 12/1992 Gotz et al. .

FOREIGN PATENT DOCUMENTS

| 0 786 519 | 7/1997 | (EP) . |
| 0 882 795 | 12/1998 | (EP) . |
| 7107981 | 4/1995 | (JP) . |
| WO 96/26276 | 8/1996 | (WO) . |
| WO 97 31114 | 8/1997 | (WO) . |

OTHER PUBLICATIONS

Lanzetta, P., Alvarez, L., Reinach, P., and Candia, O. "An Improved Assay for Nanomole Amounts of Inorganic Phosphate" *Analytical Biochemistry* 100, 95–97 (1979).

Cunningham, K., Lill, R., Crooke, E., Rice, M., Moore, K., Wickner, W., and Oliver, D. "SecA protein, a peripheral protein of the *Escherichia coli* plasma membrane, is essential for the functional binding and translocation of proOmpA" *The EMBO Journal* vol. 8 No. 3 pp. 955–959, 1989.

Lill, R., Dowhan, W., and Wickner, W. "The ATPase Activity of SecA is Regulated by Acidic Phospholipids, SecY, and the Leader and Mature Domains of Precursor Proteins" *Cell*, vol. 60, 271–280, Jan. 26, 1990.

Cabelli, R., Chen, L., Tai, P., and Oliver, D., "SecA Protein is Required for Secretory Protein Translocation into *E. coli* Membrane Vesicles" *Cell*, vol. 55, 683–692, Nov. 18, 1988.

Blaauwen, T. and Driessen, A. "Sec–dependent preprotein translocation in bacteria" *Arch Microbiol* (1996) 165: 1–8.

Wickner, W. and Leonard, M. R. "*Escherichia coli* Preprotein Translocase" *The Journal of Biological Chemistry*, vol. 271 No. 4722 Nov. 1996 pp. 29514–29516.

Snyders, S., Ramamurthy, V.. and Oliver, D. "Identifiction of a Region of interaction between *Escherichia coli* SecA and SecY Proteins" *The Journal of Biological Chemistry*, vol. 272, No. 17, Apr. 25, 1997 pp. 11302–11306.

van der Does, C., den Blaauwen, T., de Wit, J., Manting, K., Groot, N., Fekkes, P., and Driessen, A. "SecA ia an intrinsic subunit of the *Escherichia coli* preprotein translocase and exposes its carboxyl terminus to the periplasm" *Molecular Biology* (1996) 22(4), 619–629.

Chen, X., Xu, H., and Tai, P. "A Significant Fraction of Functional SecA is Permanently Embedded in the Membrane" *The Journal of Biological Chemistry*, vol. 227, No. 47, Nov. 22, 1996, pp. 29698–29706.

Breukink, E., Nouwen, N., van Raalte, A., Mizushima, S., Tommassen, J., and de Kruijff, B. "The C Terminus of SecA is Involved in Both Lipid Binding and SecB Binding" *The Journal of Biological Chemistry*, vol. 270, No. 14, Apr. 7, 1995, pp. 7902–7907.

Economou, A., Pogliano, J., Beckwith, J., Oliver, D., and Wickner, W. "SecA Membrane Cycling at SecYEG is Driven by Distinct ATP Binding and Hydrolysis Events and is Regulated by SecD and SecF" *Cell*, vol. 83, 1171–1181, Dec. 29, 1995.

Driessen, A. "SecA, the Peripheral Subunit of the *Escherichia coli* Precursor Protein Translocase, Is Functional as a Dimer" *Biochemistry* 1993, 32, 13190–13197.

van der Wolk, J., Klose, M. de Wit, J., den Blaauwen, T., Freundl, R., and Driessen, A. "Identification of the Magnesium–binding Domain of the High–affinity ATP–binding Site of the *Bacillus subtilis* and *Escherichia coli* SecA Protein" *The Journal of Biological Chemistry*, vol. 270, No. 32, Aug. 11, 1995, pp. 18975–18982.

Economou, A. and Wickner, W., "SecA Promotes Preprotein Translocation by Undergoing ATP–Driven Cycles of Membrane Insertion and Deinsertion" *Cell*, vol. 78, 835–843 Sep. 9, 1994.

Sadaie, Y., Takamatsu, H., Nakamura, K., and Yamane, K. "Sequencing reveals similarity of the wild–type div[+]gene of *Bacillus subtilis* it the *Escherichia coli* secA gene" *Gene*, 98 (1991) 101–105.

Jobling et al., Molecular Microbiology, 5(7): 1755–1767, 1991.*

Davis et al. in "Microbiology", Harper and Row, 1980 p. 267.*

Lewis, B., in "Genes IV", Oxford University Press, 1990, p. 810.*

Herzog et al., DNA and Cell Biology, 12(6): 465–471, 1993.*

Jazin et al., Regulatory Peptides 47: 247–258, 1993.*

(List continued on next page.)

*Primary Examiner*—Patricia A. Duffy
(74) *Attorney, Agent, or Firm*—Edward R. Gimmi; Thomas S. Deibert; William T. King

(57) ABSTRACT

The invention provides secA2 polypeptides and DNA (RNA) encoding secA2 polypeptides and methods for producing such polypeptides by recombinant techniques. Also provided are secA2 polynucleotides for use as diagnostic reagents.

9 Claims, No Drawings

OTHER PUBLICATIONS

Lazar et al., Molecular and Cellular Biology, 8(63): 1247–1252, 1988.*

Burgess et al., The Journal of Cell Biology, 111:2129–2138, 1990.*

Rudinger, J. in "Peptide Hormones", J.A. Parsons ed, University Park Press, Baltimore Jun. 1976 pp. 1–7.*

M Klein, et al., "Functional characterization of S. carnosus SecA protein in *E. coli* and *B. subtilis* secA mutant strains", *FEMS Microbiology*, vol. 131, pp. 271–277, Jan. 1995.

Desnottes, J–F: "New targets and strategies for the development of antibacterial agents", *Trends in Biotechnology*, vol. 14, No. 4, pp. 134–140, Apr. 1, 1996.

Sadaie Y., et al., "Sequencing reveals similiarity of the wild–type div + gene of *Bacillus subtilis* to the *Escherichia coli* secA gene", *Gene*, vol. 98, pp. 101–105, (1991).

Wickner W., et al., "*Escherichia coli* preprotein translocase", *J. Biol. Chem.*, vol. 271, pp. 29514–29516, Nov., 1996.

Oliver D.B., et al., "Azide–resistant mutants of *Escherichia coli* alter the SecA protein, an azide–sensitive component of the protein export machinery", *Proc. Natl. Acad. Sci. USA*, vol. 87, pp. 8227–8231, Nov., 1990.

* cited by examiner

SEC A2 FROM *STREPTOCOCCUS PNEUMONIAE*

FIELD OF THE INVENTION

This invention relates to newly identified polynucleotides and polypeptides, and their production and uses, as well as their variants, agonists and antagonists, and their uses. In particular, in these and in other regards, the invention relates to novel polynucleotides and polypeptides of the secA (ATPase subunit of preprotein translocase) family, hereinafter referred to as "secA2".

BACKGROUND OF THE INVENTION

It is particularly preferred to employ Staphylococcal genes and gene products as targets for the development of antibiotics. The Staphylococci make up a medically important genera of microbes. They are known to produce two types of disease, invasive and toxigenic. Invasive infections are characterized generally by abscess formation effecting both skin surfaces and deep tissues. *S. aureus* is the second leading cause of bacteremia in cancer patients. Osteomyelitis, septic arthritis, septic thrombophlebitis and acute bacterial endocarditis are also relatively common. There are at least three clinical conditions resulting from the toxigenic properties of Staphylococci. The manifestation of these diseases result from the actions of exotoxins as opposed to tissue invasion and bacteremia. These conditions include: Staphylococcal food poisoning, scalded skin syndrome and toxic shock syndrome The frequency of *Staphylococcus aureus* infections has risen dramatically in the past 20 years. This has been attributed to the emergence of multiply antibiotic resistant strains and an increasing population of people with weakened immune systems. It is no longer uncommon to isolate *Staphylococcus aureus* strains which are resistant to some or all of the standard antibiotics. This has created a demand for both new anti-microbial agents and diagnostic tests for this organism.

SecA is an essential component of the bacterial protein secretion apparatus. This enzyme has been found in a wide variety of Gram-negative and Gram-positive bacteria. SecA proteins from different bacterial species are highly homologous and there is no known mammalian homologue making SecA an ideal target for therapeutic intervention. The proposed model of SecA activity (1,2) is based on the fact that SecA binds open-folded preproteins and interacts with a specific receptor complex at the cytoplasmic membrane. ATP hydrolysis then provides the driving force for translocation of the preprotein by a unique mechanism involving transient insertion of SecA across the cytoplasmic membrane. This mechanism of bacterial translocation requires interaction of SecA with itself (SecA is functional as a dimer (3)), ATP (4), preprotein, membrane phospholipids (5,6,7), SecB (5) and the integral membrane components of the bacterial secretion apparatus (8). These numerous interactions provide us with many opportunities to inhibit the activity of this enzyme. From the above discussion we would expect inhibitors of SecA-mediated protein secretion to be broad spectrum and bactericidal without affecting eukaryotic protein secretion. For recent reviews of Sec dependent preprotein translocation see references 9 and 10.

Information on this translocation process and SecA can be found for example in: 1. Economou, A. and Wickner, W. (1994) Cell 78, 835–843; 2. Economou, A. et al. (1995) Cell 83, 1171–1181; 3. Driessen, A. J. M. (1993) Biochemistry 32, 13190–13197; 4. van der Wolk, J. P. W. et al. (1995) Journal of Biological Chemistry 270, 18975–18982; 5. Breukink, E. et al. (1995) Journal of Biological Chemistry 270, 7902–7907; 6. Chen, X et al. (1996) Journal of Biological Chemistry 271, 29698–29706; 7. van der Does, C. (1996) Molecular Microbiology 22, 619–629; 8. Snyders, S. et al. (1997) Journal of Biological Chemistry 272, 11302–11306; 9. Wickner, W and Leonard, M. R. (1996) Journal of Biological Chemistry 271,29514–29516; 10. den Blaauwen, T. and Driessen, J. M. (1996) Arch Microbiol 165, 1–8; 11. WPI Accession No: 96-425087, WO 9626276 A; and 12. WPI Accession No: 95-190181, JP 7107981 A.

Clearly, there is a need for factors, such as the novel compounds of the invention, that have a present benefit of being useful to screen compounds for antibiotic activity. Such factors are also useful to determine their role in pathogenesis of infection, dysfunction and disease. There is also a need for identification and characterization of such factors and their antagonists and agonists which can play a role in preventing, ameliorating or correcting infections, dysfunctions or diseases.

The polypeptides of the invention have amino acid sequence homology to a known *Bacillus subtilis* secA protein.

SUMMARY OF THE INVENTION

It is an object of the invention to provide polypeptides that have been identified as novel secA2 polypeptides by homology between the amino acid sequence set out in Table 1 [SEQ ID NO: 2] and a known amino acid sequence or sequences of other proteins such as *Bacillus subtilis* secA protein.

It is a further object of the invention to provide polynucleotides that encode secA2 polypeptides, particularly polynucleotides that encode the polypeptide herein designated secA2.

In a particularly preferred embodiment of the invention the polynucleotide comprises a region encoding secA2 polypeptides comprising the sequence set out in Table 1 [SEQ ID NO:1] which includes a full length gene, or a variant thereof.

In another particularly preferred embodiment of the invention there is a novel secA2 protein from *Staphylococcus aureus* comprising the amino acid sequence of Table 1 [SEQ ID NO:2], or a variant thereof.

In accordance with another aspect of the invention there is provided an isolated nucleic acid molecule encoding a mature polypeptide expressible by the *Staphylococcus aureus* WCUH 29 strain contained in the deposited strain.

A further aspect of the invention there are provided isolated nucleic acid molecules encoding secA2, particularly *Staphylococcus aureus* secA2, including mRNAs, cDNAs, genomic DNAs. Further embodiments of the invention include biologically, diagnostically, prophylactically, clinically or therapeutically useful variants thereof, and compositions comprising the same.

In accordance with another aspect of the invention, there is provided the use of a polynucleotide of the invention for therapeutic or prophylactic purposes, in particular genetic immunization. Among the particularly preferred embodiments of the invention are naturally occurring allelic variants of secA2 and polypeptides encoded thereby.

Another aspect of the invention there are provided novel polypeptides of *Staphylococcus aureus* referred to herein as secA2 as well as biologically, diagnostically, prophylactically, clinically or therapeutically useful variants thereof, and compositions comprising the same.

Among the particularly preferred embodiments of the invention are variants of secA2 polypeptide encoded by naturally occurring alleles of the secA2 gene.

In a preferred embodiment of the invention there are provided methods for producing the aforementioned secA2 polypeptides.

In accordance with yet another aspect of the invention, there are provided inhibitors to such polypeptides, useful as antibacterial agents, including, for example, antibodies.

In accordance with certain preferred embodiments of the invention, there are provided products, compositions and methods for assessing secA2 expression, treating disease, for example, disease, such as, infections of the upper respiratory tract (e.g., otitis media, bacterial tracheitis, acute epiglottitis, thyroiditis), lower respiratory (e.g., empyema, lung abscess), cardiac (e.g., infective endocarditis), gastrointestinal (e.g., secretory diarrhoea, splenic abscess, retroperitoneal abscess), CNS (e.g., cerebral abscess), eye (e.g., blepharitis, conjunctivitis, keratitis, endophthalmitis, preseptal and orbital cellulitis, darcryocystitis), kidney and urinary tract (e.g., epididymitis, intrarenal and perinephric absces, toxic shock syndrome), skin (e.g., impetigo, folliculitis, cutaneous abscesses, cellulitis, wound infection, bacterial myositis) bone and joint (e.g., septic arthritis, osteomyelitis), assaying genetic variation, and administering a secA2 polypeptide or polynucleotide to an organism to raise an immunological response against a bacteria, especially a *Staphylococcus aureus* bacteria.

In accordance with certain preferred embodiments of this and other aspects of the invention there are provided polynucleotides that hybridize to secA2 polynucleotide sequences, particularly under stringent conditions.

In certain preferred embodiments of the invention there are provided antibodies against secA2 polypeptides.

In other embodiments of the invention there are provided methods for identifying compounds which bind to or otherwise interact with and inhibit or activate an activity of a polypeptide or polynucleotide of the invention comprising: contacting a polypeptide or polynucleotide of the invention with a compound to be screened under conditions to permit binding to or other interaction between the compound and the polypeptide or polynucleotide to assess the binding to or other interaction with the compound, such binding or interaction being associated with a second component capable of providing a detectable signal in response to the binding or interaction of the polypeptide or polynucleotide with the compound; and determining whether the compound binds to or otherwise interacts with and activates or inhibits an activity of the polypeptide or polynucleotide by detecting the presence or absence of a signal generated from the binding or interaction of the compound with the polypeptide or polynucleotide.

In accordance with yet another aspect of the invention, there are provided secA2 agonists and antagonists, preferably bacteriostatic or bactericidal agonists and antagonists.

In a further aspect of the invention there are provided compositions comprising a secA2 polynucleotide or a secA2 polypeptide for administration to a cell or to a multicellular organism.

Various changes and modifications within the spirit and scope of the disclosed invention will become readily apparent to those skilled in the art from reading the following descriptions and from reading the other parts of the present disclosure.

Glossary

The following definitions are provided to facilitate understanding of certain terms used frequently herein.

"Host cell" is a cell which has been transformed or transfected, or is capable of transformation or transfection by an exogenous polynucleotide sequence.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Atschul, S. F. et al., *J. Molec. Biol.* 215: 403–410 (1990). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403–410 (1990). As an illustration, by a polynucleotide having a nucleotide sequence having at least, for example, 95% "identity" to a reference nucleotide sequence of SEQ ID NO: 1 it is intended that the nucleotide sequence of the polynucleotide is identical to the reference sequence except that the polynucleotide sequence may include up to five point mutations per each 100 nucleotides of the reference nucleotide sequence of SEQ ID NO: 1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO: 2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein.

"Polynucleotide(s)" generally refers to any polyribonucleotide or polydeoxribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, PROTEINS—STRUCTURE AND MOLECULAR PROPERTIES, 2nd Ed., T. E. Creighton, W. H. Freeman and Company, New York (1993) and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York (1983); Seifter et al., Meth. Enzymol. 182:626–646 (1990) and Rattan et al., Protein Synthesis: Posttranslational Modifications and Aging, Ann. N.Y. Acad. Sci. 663: 48–62 (1992). Polypeptides may be branched or cyclic, with or without branching. Cyclic, branched and branched circular polypeptides may result from post-translational natural processes and may be made by entirely synthetic methods, as well.

"Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

DESCRIPTION OF THE INVENTION

The invention relates to novel secA2 polypeptides and polynucleotides as described in greater detail below. In particular, the invention relates to polypeptides and polynucleotides of a novel secA2 of Staphylococcus aureus, which is related by amino acid sequence homology to

*Bacillus subtilis* secA polypeptide. The invention relates especially to secA2 having the nucleotide and amino acid sequences set out in Table 1 [SEQ ID NO: 1] and Table 1 [SEQ ID NO: 2] respectively, and to the secA2 nucleotide sequences of the DNA in the deposited strain and amino acid sequences encoded thereby.

TABLE 1 secA2 Polynucleotide and Polypeptide Sequences (A) Sequences from *Staphylococcus aureus* secA2 polynucleotide sequence [SEQ ID NO:1].
5'-ATGAAACATAAACTAGATGTTACGATAAACGAATTAAGACTAAAGTCGAT

TAGAAAAATAGTGAAACGCATCAATACATGGAGCGATGAAGTTAAATCAT

ATTCTGATGATGCGTTAAAACAAAAGACAATAGAATTTAAAGAACGTTTA

GCATCAGGAGTTGATACACTAGATACATTGTTACCTGAAGCTTATGCAGT

GGCACGTGAAGCGAGCTGGAGAGTATTAGGTATGTATCCTAAAGAAGTTC

AGTTAATCGGAGCGATTGTATTGCATGAAGGTAACATTGCGGAGATGCAA

ACAGGCGAAGGTAAAACATTAACGGCAACGATGCCTTTATATTTAAATGC

TCTTTCGGGAAAAGGAACATATTTAATTACAACGAATGATTATTTAGCGA

AGCGAGATTTTGAAGAGATGCAACCATTATATGAATGGTTAGGTTTAACT

GCTTCATTAGGTTTTGTTGATATTGTGGATTATGAGTATCAAAAAGGGGA

AAAACGTAATATATATGAACATGATATTATATATACAACTAATGGACGTC

TCGGTTTTGATTATTTAATTGATAATTTGGCTGATAGTGCGGAAGGGAAA

TTTTTACCACAATTAAATTACGGTATTATTGATGAAGTGGATTCAATCAT

TTTAGATGCTGCTCAAACACCATTAGTTATTTCGGGTGCACCAAGATTAC

AATCAAATCTATTTCATATTGTGAAAGAGTTTGTAGATACATTGATTGAA

GACGTGCATTTTAAAATGAAGAAGACCAAAAAAGAAATATGGCTGTTAAA

TCAAGGTATTGAAGCGGCACAATCATACTTTAATGTTGAAGATTTATATA

GCGAACAAGCGATGGTCCTAGTGCGTAATATTAATTTAGCACTGCGCGCA

CAATATTTGTTTGAATCTAATGTCGATTACTTTGTATATAATGGTGATAT

TGTTTTAATTGACCGTATTACAGGTCGTATGTTACCGGGAACTAAGTTGC

AAGCTGGACTTCACCAAGCTATTGAAGCGAAAGAAGGTATGGAGGTTTCA

ACAGATAAAAGTGTTATGGCAACAATTACCTTCCAGAATTTATTTAAACT

TTTTGAATCATTTTCAGGTATGACAGCTACAGGAAAATTAGGCGAATCAG

AGTTCTTTGATTTGTATTCAAAAATAGTCGTACAAGCACCAACTGATAAA

GCGATTCAACGTATCGATGAACCAGATAAAGTGTTTCGTTCAGTTGATGA

GAAAAACATCGCGATGATTCATGATATAGTTGAACTTCATGAAACGGGGC

GACCGGTTTTACTCATAACGAGAACTGCTGAAGCGGCTGAATACTTTTCC

GAAGTATTATTCCAAATGGATATTCCTAATAATTTACTCATTGCGCAAAA

TGTTGCAAAAGAAGCGCAGATGATAGCTGAAGCAGGGCAAATTGGTTCCA

TGACTGTTGCGACTAGTATGGCAGGTCGAGGCACAGATATTAAACTTGGT

GAAGGTGTCGAAGCATTAGGTGGATTAGCTGTTATTATTCATGAACATAT

GGAAAATAGCCGTGTAGACAGGCAATTACGTGGTCGTTCTGGTAGACAAG

GGGATCCGGGATCATCTTGTATATATATTTCACTAGATGATTATTTAGTT

AAGCGATGGAGCGATAGTAATTTAGCGGAAAATAATCAATTATATTCATT

AGATGCACAACGATTATCGCAAAGTAATTTGTTTAATCGCAAAGTTAAGC

TABLE 1-continued secA2 Polynucleotide and Polypeptide Sequences

AAATTGTAGTTAAAGCGCAGCGTATCTCGGAAGAACAAGGGGTTAAAGCT

CGTGAAATGGCTAATGAATTTGAAAAAAGCATTAGTATACAGCGAGATCT

TGTATACGAGGAACGCAATCGAGTTTTAGAAATAGATGATGCTGAGAATC

GAGATTTTAAAGCGTTAGCTAAAGATGTATTTGAAATGTTTGTAAATGAG

GAAAAGGTGCTAACAAAATCGCGTGTTGTCGAGTATATTTATCAAAATTT

AAGTTTCCAATTTAATAAAGATGTGGCTTGTGTTAATTTTAAAGATAAGC

AAGCAGTAGTGACATTTTTATTAGAGCAATTTGAAAAGCAATTAGCTTTG

AATCGTAAAAACATGCAAAGTGCATATTATTATAATATTTTCGTTCAAAA

AGTCTTTTTGAAAGCAATTGATTCATGTTGGTTAGAACAAGTCGACTATT

TACAACAATTAAAAGCAAGCGTTAATCAACGACAAAATGGGCAACGTAAC

GCTATTTTTGAATACCATAGAGTTGCATTAGATTCATTTGAAGTTATGAC

ACGAAATATCAAAAAAGAATGGTGAAAAATATTTGTCAAAGCATGATTA

CATTTGATAAAGAGGGTATGCCAGTTATACATTTTCCA-3'

(B) secA2 polypeptide sequence deduced from the poly-
nucleotide sequence in this table [SEQ ID NO:2].
NH$_2$-MKHKLDVTINELRLKSIRKIVKRINTWSDEVKSYSDDALKQKTIEFKERL

ASGVDTLDTLLPEAYAVAREASWRVLGMYPKEVQLIGAIVLHEGNIAEMQ

TGEGKTLTATMPLYLNALSGKGTYLITTNDYLAKRDFEEMQPLYEWLGLT

ASLGFVDIVDYETQKGEKRNIYEHDIIYTTNGRLGFDYLIDNLADSAEGK

FLPQLNYGIIDEVDSIILDAAQTPLVISGAPRLQSNLFHIVKEFVDTLIE

DVHFKMKKTKKEIWLLNQGIEAAQSYFNVEDLYSEQAMVLVRNINLALRA

QYLFESNVDYFVYNGDIVLIDRITGRMLPGTKLQAGLHQAIEAKEGMEVS

TDKSVMATITFQNLFKLFESFSGMTATGKLGESEFFDLYSKIVVQAPTDK

AIQRIDEPDKVFRSVDEKNIAMIHDIVELHETGRPVLLITRTAEAAEYFS

EVLFQMDIPNNLLIAQNVAKEAQMIAEAGQIGSMTVATSMAGRGTDIKLG

EGVEALGGLAVIIHEHMENSRVDRQLRGRSGRQGDPGDDCIYISLDDYLV

KRWSDSNLAENNQLYSLDAQRLSQSNLFNRKVKQIVVKAQRISEEQGVKA

REMANEFEKSISIQRDLVYEERNRVLEIDDAENRDFKALAKDVFEMFVNE

EKVLTKSRVVEYIYQNLSFQFNKDVACVNFKDKQAVVTFLLEQFEKQLAL

NRKNMQSAYYYNIFVQKVFLKAIDSCWLEQVDYLQQLKASVNQRQNGQRN

AIFEYHRVALDSFEVMTRNIKKRMVKNICQSMITFDKEGMPVIHFP-COOH (C) Polynucleotide sequence embodiments [SEQ ID NO:1].

X-(R$_1$)$_n$-ATGAAACATAAACTAGATGTTACGATAAACGAATTAAGACTAAAGTCGAT

TAGAAAAATAGTGAAACGCATCAATACATGGAGCGATGAAGTTAAATCAT

ATTCTGATGATGCGTTAAAACAAAAGACAATAGAATTTAAAGAACGTTTA

GCATCAGGAGTTGATACACTAGATACATTGTTACCTGAAGCTTATGCAGT

GGCACGTGAAGCGAGCTGGAGAGTATTAGGTATGTATCCTAAAGAAGTTC

AGTTAATCGGAGCGATTGTATTGCATGAAGGTAACATTGCGGAGATGCAA

ACAGGCGAAGGTAAAACATTAACGGCAACGATGCCTTTATATTTAAATGC

TABLE 1-continued secA2 Polynucleotide and Polypeptide Sequences

```
TCTTTCGGAAAAGGAACATATTTAATTACAACGAATGATTATTTAGCGA

AGCGAGATTTTGAAGAGATGCAACCATTATATGAATGGTTAGGTTTAACT

GCTTCATTAGGTTTTGTTGATATTGTGGATTATGAGTATCAAAAAGGGGA

AAAACGTAATATATGAACATGATATTATATACAACTAATGGACGTC

TCGGTTTTGATTATTTAATTGATAATTTGGCTGATAGTGCGGAAGGGAAA

TTTTTACCACAATTAAATTACGGTATTATTGATGAAGTGGATTCAATCAT

TTTAGATGCTGCTCAAACACCATTAGTTATTTCGGGTGCACCAAGATTAC

AATCAAATCTATTTCATATTGTGAAAGAGTTTGTAGATACATTGATTGAA

GACGTGCATTTTAAAATGAAGAAGACCAAAAAAGAAATATGGCTGTTAAA

TCAAGGTATTGAAGCGGCACAATCATACTTTAATGTTGAAGATTTATATA

GCGAACAAGCGATGGTCCTAGTGCGTAATATTAATTTAGCACTGCGCGCA

CAATATTTGTTTGAATCTAATGTCGATTACTTTGTATATAATGGTGATAT

TGTTTTAATTGACCGTATTACAGGTCGTATGTTACCGGGAACTAAGTTGC

AAGCTGGACTTCACCAAGCTATTGAAGCGAAAGAAGGTATGGAGGTTTCA

ACAGATAAAAGTGTTATGGCAACAATTACCTTCCAGAATTTATTTAAACT

TTTTGAATCATTTTCAGGTATGACAGCTACAGGAAAATTAGGCGAATCAG

AGTTCTTTGATTTGTATTCAAAAATAGTCGTACAAGCACCAACTGATAAA

GCGATTCAACGTATCGATGAACCAGATAAAGTGTTTCGTTCAGTTGATGA

GAAAAACATCGCGATGATTCATGATATAGTTGAACTTCATGAAACGGGGC

GACCGGTTTTACTCATAACGAGAACTGCTGAAGCGGCTGAATACTTTTCC

GAAGTATTATTCCAAATGGATATTCCTAATAATTTACTCATTGCGCAAAA

TGTTGCAAAAGAAGCGCAGATGATAGCTGAAGCAGGGCAAATTGGTTCCA

TGACTGTTGCGACTAGTATGGCAGGTCGAGGCACAGATATTAAACTTGGT

GAAGGTGTCGAAGCATTAGGTGGATTAGCTGTTATTATTCATGAACATAT

GGAAAATAGCCGTGTAGACAGGCAATTACGTGGTCGTTCTGGTAGACAAG

GGGATCCGGGATCATCTTGTATATATATTTCACTAGATGATTATTTAGTT

AAGCGATGGAGCGATAGTAATTTAGCGGAAAATAATCAATTATATTCATT

AGATGCACAACGATTATCGCAAAGTAATTTGTTTAATCGCAAAGTTAAGC

AAATTGTAGTTAAAGCGCAGCGTATCTCGGAAGAACAAGGGGTTAAAGCT

CGTGAAATGGCTAATGAATTTGAAAAAAGCATTAGTATACAGCGAGATCT

TGTATACGAGGAACGCAATCGAGTTTTAGAAATAGATGATGCTGAGAATC

GAGATTTTAAAGCGTTAGCTAAAGATGTATTTGAAATGTTTGTAAATGAG

GAAAAGGTGCTAACAAAATCGCGTGTTGTCGAGTATATTTATCAAAATTT

AAGTTTCCAATTTAATAAAGATGTGGCTTGTGTTAATTTTAAAGATAAGC

AAGCAGTAGTGACATTTTTATTAGAGCAATTTGAAAAGCAATTAGCTTTG

AATCGTAAAAACATGCAAAGTGCATATTATTATAATATTTTCGTTCAAAA

AGTCTTTTTGAAAGCAATTGATTCATGTTGGTTAGAACAAGTCGACTATT

TACAACAATTAAAAGCAAGCGTTAATCAACGACAAAATGGGCAACGTAAC
```

TABLE 1-continued secA2 Polynucleotide and Polypeptide Sequences

GCTATTTTTGAATACCATAGAGTTGCATTAGATTCATTTGAAGTTATGAC

ACGAAATATCAAAAAAAGAATGGTGAAAAATATTTGTCAAAGCATGATTA

CATTTGATAAAGAGGGTATGCCAGTTATACATTTTCCA-$(R_2)_n$-Y (D) Polypeptide sequence embodiments[SEQ ID NO:2].

X-$(R_1)_n$-MKHKLDVTINELRLKSIRKIVKRINTWSDEVKSYSDDALKQKTIEFKERL

ASGVDTLDTLLPEAYAVAREASWRVLGMYPKEVQLIGAIVLHEGNIAEMQ

TGEGKTLTATMPLYLNALSGKGTYLITTNDYLAKRDFEEMQPLYEWLGLT

ASLGFVDIVDYEYQKGEKRNIYEHDIIYTTNGRLGFDYLIDNLADSAEGK

FLPQLNYGIIDEVDSIILDAAQTPLVISGAPRLQSNLFHIVKEFVDTLIE

DVHFKMKKTKKEIWLLNQGIEAAQSYFNVEDLYSEQAMVLVRNINLALRA

QYLFESNVDYFVYNGDIVLIDRITGRMLPGTKLQAGLHQAIEAKEGMEVS

TDKSVMATITFQNLFKLFESFSGMTATGKLGESEFFDLYSKIVVQAPTDK

AIQRIDEPDKVFRSVDEKNIAMIHDIVELHETGRPVLLITRTAEAAEYFS

EVLFQMDIPNNLLIAQNVAKEAQMIAEAGQIGSMTVATSMAGRGTDIKLG

EGVEALGGLAVIIHEHMENSRVDRQLRGRSGRQGDPGSSCIYISLDDYLV

KRWSDSNLAENNQLYSLDAQRLSQSNLFNRKVKQIVVKAQRISEEQGVKA

REMANEDEKSISIQRDLVYEERNRVLEIDDAENRDFKALAKDVFEMFVNE

EKVLTKSRVVEYIYQNLSFQFNKDVACVNFKDKQAVVTFLLEQFEKQLAL

NRKNMQSAYYYNIFVQKVFLKAIDSCWLEQVDYLQQLKASVNQRQNGQRN

AIFEYHRVALDSFEVMTRNIKKRMVKNICQSMITFDKEGMPVIHFP-$(R_2)_n$-Y (E) Sequences from *Staphylococcus aureus* secA2
polynucleotide ORF sequence[SEQ ID NO:3].

```
  5'-1 GTTAATCAAG TATCGAAGCG GAACAATCAT ACTTTAATGT TGAAGATTTA
    51 TATNGCGAAC AAGCGATGGT CCTAGTGCGT AATATTAATT TAGCACTGCG
   101 CGCACAATAT TTGTTNGNAT CTNATGTCGA TTACTTTGTA TATNNTGGTG
   151 ATATTGTTTT AACTGACCGC ATTACAGGTC GTNTGTTACC GGNAACTAAG
   201 TTGCAAGCTG GACTTCACCA NGCTATTGAA GCGAAAGAAG GTATGGAGGT
   251 TTCAACAGAT AAAAGTGTTA TGCCAACCAA TTACCCTTCC AGAATTTATT
   301 TAAACTTTTT GAATCAATTT TCAGGTATGA CAAGCTACAG GAAAATTAGG
   351 CGAATCAGAG TTCTTTGATT TGTATTCANA AATAGTCGTA CAAGCACCCA
   401 ACTGATAAAG CGATTCAACG TATCGATGAA CCAGATAAAG TGTTTCGTTC
   451 AGTTGATGAG AAAAACATCG CGATGATTCA TTGATATAGT TGAACTTCAT
   501 GANNCGGGGC CGACCGGTTT TACCTCATAA CCGAGNACTG CTGAAGCGGC
   551 TTGAATACTT TTCNGAAGTA TTATTCCAAA TGGATATTCC TAATAATTTA
   601 CTCATTGCGC AAAATGTTCC AAAAGAAGCG CAGATGATAG CTGAAGCAGG
   651 CCAAATTGGT TCCATGACTG TTGCGACTAG TATGGCAGGT CGAGGCACAG
   701 ATATTAAACT TGGTGAAGGT GTCGAAGCAT TAGCTGGATT AGCTGTTATT
   751 ATTCATGAAC ATATGGAAAA TAGCCGTGTA GACAGGCAAT TACGTGGTCG
```

TABLE 1-continued secA2 Polynucleotide and Polypeptide Sequences

```
 801 TTCTGGTAGA CAAGGGGATC CGGGATCATC TTGTATATAT ATTTCACTAG

851 ATGATTATTT AGNTAAGCGA TGGAGCGATA GTAATTTAGC GGAAAATAAT

901 CAATTATATT CANTAGATGC ACAACGATTA TCGCAAAGTA ATTTGTTTAA

951 TCGNAAAGTT AAGCAAATTG TAGTTAAAGC GCAGCGTATC TCGGAAAGAA

1001 CAAGGGGTTA AAGCTCGGTG AAATGGCTTA ATTGAATTTG NNAAAAAGCA

1051 TNAGTATTCA GCGAAGATCT TNGTATTTAC GANGGAACGC AAATCCGAGT

1101 TTTTAGAAAT TAGATTGATG CTGAGAATCC NAGATTTTTA ANGCGGTTAG

1151 CTTAAAGATT GTATTTGAAA TNGTTTGGGG NAATGANGGA AANGGTGCTA

1201 ACAAAATCGC GNGTTGGGCG AGTATATTTT ATCAAAAATT TAAGTTNCCA

1251 ATTTAATAAA GATGTGGCTT GTGTTAATTT TAAAGATAAG CAAGCAGNAG

1301 TGACATTTTT ATTAGAGCAA TTTGAAAAGC AATTAGCTTT GGANTCCGTA

1351 AAAACATGCA ANGNGCATAT TATTATAATA TTNCCGGCCA AAANGTCTTT

1401 NGGGAAAGCA ATTGATNCAA GTTGGGGTTA GGAACAAGTC GGCTTTTNAC

1451 AACAANTTAA NAGCAAGCGN TAATCAAACG ACAAAANTGG CAACCT-3'
```

(F) secA2 polypeptide sequence deduced from the polynucleotide ORF sequence in this table [SEQ ID NO:4].

```
NH2-1  MDIPNNLLIA QNVPKEAQMI AEAGQIGSMT VATSMAGRGT DIKLGEGVEA

51  LAGLAVIIHE HMENSRVDRQ LRGRSGRQGD PGSSCIYISL DDYLXKRWSD

101  SNLAENNQLY SXDAQRLSQS NLFNRKVKQI VVKAQRISER TRG-COOH
```

Deposited materials

A deposit containing a *Staphylococcus aureus* WCUH 29 strain has been deposited with the National Collections of Industrial and Marine Bacteria Ltd. (herein "NCIMB"), 23 St. Machar Drive, Aberdeen AB2 1RY, Scotland on Sep. 11, 1995 and assigned NCIMB Deposit No. 40771, and is referred to as *Staphylococcus aureus* WCUH29 on deposit. The *Staphylococcus aureus* strain deposit is referred to herein as "the deposited strain" or as "the DNA of the deposited strain."

The deposited strain contains the full length secA2 gene. The sequence of the polynucleotides contained in the deposited strain, as well as the amino acid sequence of the polypeptide encoded thereby, are controlling in the event of any conflict with any description of sequences herein.

The deposit of the deposited strain has been made under the terms of the Budapest Treaty on the International Recognition of the Deposit of Micro-organisms for Purposes of Patent Procedure. The strain will be irrevocably and without restriction or condition released to the public upon the issuance of a patent. The deposited strain is provided merely as convenience to those of skill in the art and is not an admission that a deposit is required for enablement, such as that required under 35 U.S.C. §112.

A license may be required to make, use or sell the deposited strain, and compounds derived therefrom, and no such license is hereby granted.

Polypeptides

The polypeptides of the invention include the polypeptide of Table 1 [SEQ ID NO:2] (in particular the mature polypeptide) as well as polypeptides and fragments, particularly those which have the biological activity of secA2, and also those which have at least 70% identity to a polypeptide of Table 1 [SEQ ID NOS:2 and 4] or the relevant portion, preferably at least 80% identity to a polypeptide of Table 1 [SEQ ID NOS:2 and 4], and more preferably at least 90% similarity (more preferably at least 90% identity) to a polypeptide of Table 1 [SEQ ID NOS:2 and 4] and still more preferably at least 95% similarity (still more preferably at least 95% identity) to a polypeptide of Table 1 [SEQ ID NOS:2 and 4] and also include portions of such polypeptides with such portion of the polypeptide generally containing at least 30 amino acids and more preferably at least 50 amino acids.

The invention also includes polypeptides of the formula set forth in Table 1 (D) [SEQ ID NO:2] wherein, at the amino terminus, X is hydrogen, and at the carboxyl terminus, Y is hydrogen or a metal, $R_1$ and $R_2$ is any amino acid residue, and n is an integer between 1 and 1000. Any stretch of amino acid residues denoted by either R group, where R is greater than 1, may be either a heteropolymer or a homopolymer, preferably a heteropolymer.

A fragment is a variant polypeptide having an amino acid sequence that entirely is the same as part but not all of the amino acid sequence of the aforementioned polypeptides. As with secA2 polypeptides fragments may be "free-standing," or comprised within a larger polypeptide of which they form a part or region, most preferably as a single continuous region, a single larger polypeptide.

Preferred fragments include, for example, truncation polypeptides having a portion of an amino acid sequence of Table 1 [SEQ ID NOS:2 and 4], or of variants thereof, such as a continuous series of residues that includes the amino terminus, or a continuous series of residues that includes the carboxyl terminus. Degradation forms of the polypeptides of the invention in a host cell, particularly a *Staphylococcus aureus*, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Also preferred are biologically active fragments which are those fragments that mediate activities of secA2, including those with a similar activity or an improved activity, or with a decreased undesirable activity. Also included are those fragments that are antigenic or immunogenic in an animal, especially in a human. Particularly preferred are fragments comprising receptors or domains of enzymes that confer a function essential for viability of *Staphylococcus aureus* or the ability to initiate, or maintain cause disease in an individual, particularly a human.

Variants that are fragments of the polypeptides of the invention may be employed for producing the corresponding full-length polypeptide by peptide synthesis; therefore, these variants may be employed as intermediates for producing the full-length polypeptides of the invention.

Polynucleotides

Another aspect of the invention relates to isolated polynucleotides, including the full length gene, that encode the secA2 polypeptide having a deduced amino acid sequence of Table 1 [SEQ ID NOS:2 and 4] and polynucleotides closely related thereto and variants thereof.

Using the information provided herein, such as a polynucleotide sequence set out in Table 1 [SEQ ID NOS:1 and 3], a polynucleotide of the invention encoding secA2 polypeptide may be obtained using standard cloning and screening methods, such as those for cloning and sequencing chromosomal DNA fragments from bacteria using *Staphylococcus aureus* WCUH 29 cells as starting material, followed by obtaining a full length clone. For example, to obtain a polynucleotide sequence of the invention, such as a sequence given in Table 1 [SEQ ID NOS:1 and 3], typically a library of clones of chromosomal DNA of *Staphylococcus aureus* WCUH 29 in *E.coli* or some other suitable host is probed with a radiolabeled oligonucleotide, preferably a 17-mer or longer, derived from a partial sequence. Clones carrying DNA identical to that of the probe can then be distinguished using stringent conditions. By sequencing the individual clones thus identified with sequencing primers designed from the original sequence it is then possible to extend the sequence in both directions to determine the full gene sequence. Conveniently, such sequencing is performed using denatured double stranded DNA prepared from a plasmid clone. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Illustrative of the invention, the polynucleotide set out in Table 1 [SEQ ID NO:1] was discovered in a DNA library derived from *Staphylococcus aureus* WCUH 29.

The DNA sequence set out in Table 1 [SEQ ID NOS:1] contains an open reading frame encoding a protein having about the number of amino acid residues set forth in Table 1 [SEQ ID NO:2] with a deduced molecular weight that can be calculated using amino acid residue molecular weight values well known in the art. The polynucleotide of SEQ ID NO: 1, between nucleotide number 1 through number 2388 encodes the polypeptide of SEQ ID NO:2. The stop codon begins at nucleotide number 2389 of SEQ ID NO:1.12388.

The secA2 protein of the invention is structurally related to other proteins of the secA (ATPase subunit of preprotein translocase) family, as shown by the results of sequencing the DNA encoding secA2 of the deposited strain. The protein exhibits greatest homology to *Bacillus subtilis* secA protein among known proteins. The secA2 protein of Table 1 [SEQ ID NO:2] has about 39% identity over its entire length and about 62% similarity over its entire length with the amino acid sequence of *Bacillus subtilis* secA polypeptide.

The invention provides a polynucleotide sequence identical over its entire length to the coding sequence in Table 1 [SEQ ID NO:1]. Also provided by the invention is the coding sequence for the mature polypeptide or a fragment thereof, by itself as well as the coding sequence for the mature polypeptide or a fragment in reading frame with other coding sequence, such as those encoding a leader or secretory sequence, a pre-, or pro- or prepro- protein sequence. The polynucleotide may also contain non-coding sequences, including for example, but not limited to non-coding 5' and 3' sequences, such as the transcribed, non-translated sequences, termination signals, ribosome binding sites, sequences that stabilize mRNA, introns, polyadenylation signals, and additional coding sequence which encode additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci., USA* 86. 821–824 (1989), or an HA tag (Wilson et al., *Cell* 37: 767 (1984). Polynucleotides of the invention also include, but are not limited to, polynucleotides comprising a structural gene and its naturally associated sequences that control gene expression.

A preferred embodiment of the invention is a polynucleotide of comprising nucleotide 1 to 2388 or 2389 set forth in SEQ ID NO:1 of Table 1 which encode the secA2 polypeptide.

The invention also includes polynucleotides of the formula set forth in Table 1 (C)[SEQ ID NO:1] wherein, at the 5' end of the molecule, X is hydrogen, and at the 3' end of the molecule, Y is hydrogen or a metal, $R_1$ and $R_2$ is any nucleic acid residue, and n is an integer between 1 and 1000. Any stretch of nucleic acid residues denoted by either R group, where R is greater than 1, may be either a heteropolymer or a homopolymer, preferably a heteropolymer.

The term "polynucleotide encoding a polypeptide" as used herein encompasses polynucleotides that include a sequence encoding a polypeptide of the invention, particularly a bacterial polypeptide and more particularly a polypeptide of the *Staphylococcus aureus* secA2 having the amino acid sequence set out in Table 1 [SEQ ID NO:2 or SEQ ID NO: 4]. The term also encompasses polynucleotides that include a single continuous region or discontinuous regions encoding the polypeptide (for example, interrupted by integrated phage or an insertion sequence or editing) together with additional regions, that also may contain coding and/or non-coding sequences.

The invention further relates to variants of the polynucleotides described herein that encode for variants of the polypeptide having the deduced amino acid sequence of Table 1 [SEQ ID NO:2 or SEQ ID NO: 4]. Variants that are fragments of the polynucleotides of the invention may be used to synthesize full-length polynucleotides of the invention.

Further particularly preferred embodiments are polynucleotides encoding secA2 variants, that have the amino acid sequence of secA2 polypeptide of Table 1 [SEQ ID NO:2] in which several, a few, 5 to 10, 1 to 5, 1 to 3, 2, 1 or no amino acid residues are substituted, deleted or added, in any combination. Especially preferred among these are silent substitutions, additions and deletions, that do not alter the properties and activities of secA2.

Further preferred embodiments of the invention are polynucleotides that are at least 70% identical over their entire length to a polynucleotide encoding secA2 polypeptide having an amino acid sequence set out in Table 1 [SEQ ID NOS:2 and 4], and polynucleotides that are complementary to such polynucleotides. Alternatively, most highly preferred are polynucleotides that comprise a region that is at least 80% identical over its entire length to a polynucleotide encoding secA2 polypeptide of the deposited strain and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides that encode polypeptides that retain substantially the same biological function or activity as the mature polypeptide encoded by the DNA of Table 1 [SEQ ID NO:1].

The invention further relates to polynucleotides that hybridize to the herein above-described sequences. In this regard, the invention especially relates to polynucleotides that hybridize under stringent conditions to the herein above-described polynucleotides. As herein used, the terms "stringent conditions" and "stringent hybridization conditions" mean hybridization will occur only if there is at least 95% and preferably at least 97% identity between the sequences. An example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein.

The invention also provides a polynucleotide consisting essentially of a polynucleotide sequence obtainable by screening an appropriate library containing the complete gene for a polynucleotide sequence set forth in SEQ ID NO:1 or SEQ ID NO:3 under stringent hybridization conditions with a probe having the sequence of said polynucleotide sequence set forth in SEQ ID NO:1 or SEQ ID NO: 3 or a fragment thereof; and isolating said DNA sequence. Fragments useful for obtaining such a polynucleotide include, for example, probes and primers described elsewhere herein.

As discussed additionally herein regarding polynucleotide assays of the invention, for instance, polynucleotides of the invention as discussed above, may be used as a hybridization probe for RNA, cDNA and genomic DNA to isolate full-length cDNAs and genomic clones encoding secA2 and to isolate cDNA and genomic clones of other genes that have a high sequence similarity to the secA2 gene. Such probes generally will comprise at least 15 bases. Preferably, such probes will have at least 30 bases and may have at least 50 bases. Particularly preferred probes will have at least 30 bases and will have 50 bases or less.

For example, the coding region of the secA2 gene may be isolated by screening using the DNA sequence provided in SEQ ID NO: 1 or SEQ ID NO: 3 to synthesize an oligonucleotide probe. A labeled oligonucleotide having a sequence complementary to that of a gene of the invention is then used to screen a library of cDNA, genomic DNA or mRNA to determine which members of the library the probe hybridizes to.

The polynucleotides and polypeptides of the invention may be employed, for example, as research reagents and materials for discovery of treatments of and diagnostics for disease, particularly human disease, as further discussed herein relating to polynucleotide assays.

Polynucleotides of the invention that are oligonucleotides derived from the sequences of SEQ ID NOS:1 and/or 2 may be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that may encode a polypeptide that is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

Vectors, host cells, expression

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

For recombinant production, host cells can be genetically engineered to incorporate expression systems or portions thereof or polynucleotides of the invention. Introduction of a polynucleotide into the host cell can be effected by methods described in many standard laboratory manuals, such as Davis et al., BASIC METHODS IN MOLECULAR BIOLOGY, (1986) and Sambrook et al., MOLECULAR CLONING: A LABORATORY MANUAL, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as streptococci, staphylococci, enterococci E. coli, streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

A great variety of expression systems can be used to produce the polypeptides of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., MOLECULAR CLONING, A LABORATORY MANUAL, (supra).

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Most preferably, high performance liquid chromatography is employed for purification. Well known techniques for refolding protein may be employed to regenerate active conformation when the polypeptide is denatured during isolation and or purification.

Diagnostic Assays

This invention is also related to the use of the secA2 polynucleotides of the invention for use as diagnostic reagents. Detection of secA2 in a eukaryote, particularly a mammal, and especially a human, will provide a diagnostic method for diagnosis of a disease. Eukaryotes (herein also "individual(s)"), particularly mammals, and especially humans, infected with an organism comprising the secA2 gene may be detected at the nucleic acid level by a variety of techniques.

Nucleic acids for diagnosis may be obtained from an infected individual's cells and tissues, such as bone, blood, muscle, cartilage, and skin. Genomic DNA may be used directly for detection or may be amplified enzymatically by using PCR or other amplification technique prior to analysis. RNA or cDNA may also be used in the same ways. Using amplification, characterization of the species and strain of prokaryote present in an individual, may be made by an analysis of the genotype of the prokaryote gene. Deletions and insertions can be detected by a change in size of the amplified product in comparison to the genotype of a reference sequence. Point mutations can be identified by hybridizing amplified DNA to labeled secA2 polynucleotide sequences. Perfectly matched sequences can be distinguished from mismatched duplexes by RNase digestion or by differences in melting temperatures. DNA sequence differences may also be detected by alterations in the electrophoretic mobility of the DNA fragments in gels, with or without denaturing agents, or by direct DNA sequencing. See, e.g., Myers et al., Science, 230: 1242 (1985). Sequence changes at specific locations also may be revealed by nuclease protection assays, such as RNase and S1 protection or a chemical cleavage method. See, e.g., Cotton et al., Proc. Natl. Acad. Sci., USA, 85. 4397–4401 (1985).

Cells carrying mutations or polymorphisms in the gene of the invention may also be detected at the DNA level by a variety of techniques, to allow for serotyping, for example. For example, RT-PCR can be used to detect mutations. It is particularly preferred to used RT-PCR in conjunction with automated detection systems, such as, for example, GeneScan. RNA or cDNA may also be used for the same purpose, PCR or RT-PCR. As an example, PCR primers complementary to a nucleic acid encoding secA2 can be used to identify and analyze mutations. Examples of representative primers are shown below in Table 2.

TABLE 2

Primers for amplification of secA2 polynucleotides

| SEQ ID NO | PRIMER SEQUENCE |
|---|---|
| 5 | 5'-ATGAAACATA AACTAGATGT TACG-3' |
| 6 | 5'-TGGAAAATGT ATAACTGGCA TACC-3' |

The invention further provides these primers with 1, 2, 3 or 4 nucleotides removed from the 5' and/or the 3' end. These primers may be used for, among other things, amplifying secA2 DNA isolated from a sample derived from an individual. The primers may be used to amplify the gene isolated from an infected individual such that the gene may then be subject to various techniques for elucidation of the DNA sequence. In this way, mutations in the DNA sequence may be detected and used to diagnose infection and to serotype and/or classify the infectious agent.

The invention further provides a process for diagnosing, disease, preferably bacterial infections, more preferably infections by Staphylococcus aureus, and most preferably disease, such as, infections of the upper respiratory tract (e.g., otitis media, bacterial tracheitis, acute epiglottitis, thyroiditis), lower respiratory (e.g., empyema, lung abscess), cardiac (e.g., infective endocarditis), gastrointestinal (e.g., secretory diarrhoea, splenic absces, retroperitoneal abscess), CNS (e.g., cerebral abscess), eye (e.g., blepharitis, conjunctivitis, keratitis, endophthalmitis, preseptal and orbital cellulitis, darcryocystitis), kidney and urinary tract (e.g., epididymitis, intrarenal and perinephric absces, toxic shock syndrome), skin (e.g., impetigo, folliculitis, cutaneous abscesses, cellulitis, wound infection, bacterial myositis) bone and joint (e.g., septic arthritis, osteomyelitis), comprising determining from a sample derived from an individual a increased level of expression of polynucleotide having the sequence of Table 1 [SEQ ID NO: 1 or SEQ ID NO: 3]. Increased or decreased expression of secA2 polynucleotide can be measured using any on of the methods well known in the art for the quantation of polynucleotides, such as, for example, amplification, PCR, RT-PCR, RNase protection, Northern blotting and other hybridization methods.

In addition, a diagnostic assay in accordance with the invention for detecting over-expression of secA2 protein compared to normal control tissue samples may be used to detect the presence of an infection, for example. Assay techniques that can be used to determine levels of a secA2 protein, in a sample derived from a host are well-known to those of skill in the art. Such assay methods include radioimmunoassays, competitive-binding assays, Western Blot analysis and ELISA assays.

Antibodies

The polypeptides of the invention or variants thereof, or cells expressing them can be used as an immunogen to produce antibodies immunospecific for such polypeptides. "Antibodies" as used herein includes monoclonal and polyclonal antibodies, chimeric, single chain, simianized antibodies and humanized antibodies, as well as Fab fragments, including the products of an Fab immunolglobulin expression library.

Antibodies generated against the polypeptides of the invention can be obtained by administering the polypeptides or epitope-bearing fragments, analogues or cells to an animal, preferably a nonhuman, using routine protocols. For preparation of monoclonal antibodies, any technique known in the art that provides antibodies produced by continuous cell line cultures can be used. Examples include various techniques, such as those in Kohler, G. and Milstein, C., Nature 256: 495–497 (1975); Kozbor et al., Immunology Today 4: 72 (1983); Cole et al., pg. 77–96 in MONOCLONAL ANTIBODIES AND CANCER THERAPY, Alan R. Liss, Inc. (1985).

Techniques for the production of single chain antibodies (U.S. Pat. No. 4,946,778) can be adapted to produce single chain antibodies to polypeptides of this invention. Also, transgenic mice, or other organisms such as other mammals, may be used to express humanized antibodies.

Alternatively phage display technology may be utilized to select antibody genes with binding activities towards the polypeptide either from repertoires of PCR amplified v-genes of lymphocytes from humans screened for possessing anti-secA2 or from naive libraries (McCafferty, J. et al., (1990), Nature 348, 552–554; Marks, J. et al., (1992) Biotechnology 10, 779–783). The affinity of these antibodies can also be improved by chain shuffling (Clackson, T. et al., (1991) Nature 352, 624–628).

If two antigen binding domains are present each domain may be directed against a different epitope—termed 'bispecific' antibodies.

The above-described antibodies may be employed to isolate or to identify clones expressing the polypeptides to purify the polypeptides by affinity chromatography.

Thus, among others, antibodies against secA2-polypeptide may be employed to treat infections, particularly bacterial infections and especially disease, such as, infections of the upper respiratory tract (e.g., otitis media, bacterial tracheitis, acute epiglottitis, thyroiditis), lower respiratory (e.g., empyema, lung abscess), cardiac (e.g., infective endocarditis), gastrointestinal (e.g., secretory diarrhoea, splenic absces, retroperitoneal abscess), CNS (e.g., cerebral abscess), eye (e.g., blepharitis, conjunctivitis, keratitis, endophthalmitis, preseptal and orbital cellulitis, darcryocystitis), kidney and urinary tract (e.g., epididymitis, intrarenal and perinephric absces, toxic shock syndrome), skin (e.g., impetigo, folliculitis, cutaneous abscesses, cellulitis, wound infection, bacterial myositis) bone and joint (e.g., septic arthritis, osteomyelitis).

Polypeptide variants include antigenically, epitopically or immunologically equivalent variants that form a particular aspect of this invention. The term "antigenically equivalent derivative" as used herein encompasses a polypeptide or its equivalent which will be specifically recognized by certain antibodies which, when raised to the protein or polypeptide according to the invention, interfere with the immediate physical interaction between pathogen and mammalian host. The term "immunologically equivalent derivative" as used herein encompasses a peptide or its equivalent which when used in a suitable formulation to raise antibodies in a vertebrate, the antibodies act to interfere with the immediate physical interaction between pathogen and mammalian host.

The polypeptide, such as an antigenically or immunologically equivalent derivative or a fusion protein thereof is used as an antigen to immunize a mouse or other animal such as a rat or chicken. The fusion protein may provide stability to the polypeptide. The antigen may be associated, for example by conjugation, with an immunogenic carrier protein for example bovine serum albumin (BSA) or keyhole limpet haemocyanin (KLH). Alternatively a multiple antigenic peptide comprising multiple copies of the protein or polypeptide, or an antigenically or immunologically equivalent polypeptide thereof may be sufficiently antigenic to improve immunogenicity so as to obviate the use of a carrier.

Preferably, the antibody or variant thereof is modified to make it less immunogenic in the individual. For example, if the individual is human the antibody may most preferably be "humanized"; where the complimentarity determining region(s) of the hybridoma-derived antibody has been transplanted into a human monoclonal antibody, for example as described in Jones, P. et al. (1986), Nature 321, 522–525 or Tempest et al., (1991) Biotechnology 9, 266–273.

The use of a polynucleotide of the invention in genetic immunization will preferably employ a suitable delivery method such as direct injection of plasmid DNA into muscles (Wolff et al., Hum Mol Genet 1992, 1:363, Manthorpe et al., Hum. Gene Ther. 1963:4, 419), delivery of DNA complexed with specific protein carriers (Wu et al., J Biol Chem. 1989: 264,16985), coprecipitation of DNA with calcium phosphate (Benvenisty & Reshef, PNAS USA, 1986:83,9551), encapsulation of DNA in various forms of liposomes (Kaneda et al., Science 1989:243,375), particle bombardment (Tang et al., Nature 1992, 356:152, Eisenbraun et al., DNA Cell Biol 1993, 12:791) and in vivo infection using cloned retroviral vectors (Seeger et al., PNAS USA 1984:81,5849).

Antagonists and agonists—assays and molecules

Polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al., *Current Protocols in Immunology* 1(2): Chapter 5 (1991).

The invention also provides a method of screening compounds to identify those which enhance (agonist) or block (antagonist) the action of secA2 polypeptides or polynucleotides, particularly those compounds that are bacteriostatic and/or bactericidal. The method of screening may involve high-throughput techniques. For example, to screen for agonists or antagonists, a synthetic reaction mix, a cellular compartment, such as a membrane, cell envelope or cell wall, or a preparation of any thereof, comprising secA2 polypeptide and a labeled substrate or ligand of such polypeptide is incubated in the absence or the presence of a candidate molecule that may be a secA2 agonist or antagonist. The ability of the candidate molecule to agonize or antagonize the secA2 polypeptide is reflected in decreased binding of the labeled ligand or decreased production of product from such substrate. Molecules that bind gratuitously, i.e., without inducing the effects of secA2 polypeptide are most likely to be good antagonists. Molecules that bind well and increase the rate of product production from substrate are agonists. Detection of the rate or level of production of product from substrate may be enhanced by using a reporter system. Reporter systems that may be useful in this regard include but are not limited to colorimetric labeled substrate converted into product, a reporter gene that is responsive to changes in secA2 polynucleotide or polypeptide activity, and binding assays known in the art.

Another example of an assay for secA2 antagonists is a competitive assay that combines secA2 and a potential antagonist with secA2-binding molecules, recombinant secA2 binding molecules, natural substrates or ligands, or substrate or ligand mimetics, under appropriate conditions for a competitive inhibition assay. The secA2 protein can be labeled, such as by radioactivity or a colorimetric compound, such that the number of secA2 molecules bound to a binding molecule or converted to product can be determined accurately to assess the effectiveness of the potential antagonist.

Potential antagonists include small organic molecules, peptides, polypeptides and antibodies that bind to a polynucleotide or polypeptide of the invention and thereby inhibit or extinguish its activity. Potential antagonists also may be small organic molecules, a peptide, a polypeptide such as a closely related protein or antibody that binds the same sites on a binding molecule, such as a binding molecule, without inducing secA2-induced activities, thereby preventing the action of secA2 by excluding secA2 from binding.

Potential antagonists include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, *J. Neurochem.* 56: 560 (1991); *OLIGODEOXYNUCLEOTIDES AS ANTISENSE INHIBITORS OF GENE EXPRESSION*, CRC Press, Boca Raton, Fla. (1988), for a description of these molecules). Preferred potential antagonists include compounds related to and variants of secA2.

Each of the DNA sequences provided herein may be used in the discovery and development of antibacterial compounds. The encoded protein, upon expression, can be used as a target for the screening of antibacterial drugs. Additionally, the DNA sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide or inhibitor of the invention to interfere with the initial physical interaction between a pathogen and mammalian host responsible for sequelae of infection. In particular the molecules of the invention may be used: in the prevention of adhesion of bacteria, in particular gram positive bacteria, to mammalian extracellular matrix proteins on in-dwelling devices or to extracellular matrix proteins in wounds; to block secA2 protein-mediated mammalian cell invasion by, for example, initiating phosphorylation of mammalian tyrosine kinases (Rosenshine et al., *Infect. Immun.* 60:2211 (1992); to block bacterial adhesion between mammalian extracellular matrix proteins and bacterial secA2 proteins that mediate tissue damage and; to block the normal progression of pathogenesis in infections initiated other than by the implantation of in-dwelling devices or by other surgical techniques.

The antagonists and agonists of the invention may be employed, for instance, to inhibit and treat disease, such as, infections of the upper respiratory tract (e.g., otitis media, bacterial tracheitis, acute epiglottitis, thyroiditis), lower respiratory (e.g., empyema, lung abscess), cardiac (e.g., infective endocarditis), gastrointestinal (e.g., secretory diarrhoea, splenic abscess, retroperitoneal abscess), CNS (e.g., cerebral abscess), eye (e.g., blepharitis, conjunctivitis, keratitis, endophthalmitis, preseptal and orbital cellulitis, darcryocystitis), kidney and urinary tract (e.g., epididymitis, intrarenal and perinephric absces, toxic shock syndrome), skin (e.g., impetigo, folliculitis, cutaneous abscesses, cellulitis, wound infection, bacterial myositis) bone and joint (e.g., septic arthritis, osteomyelitis).

Vaccines

Another aspect of the invention relates to a method for inducing an immunological response in an individual, particularly a mammal which comprises inoculating the individual with secA2, or a fragment or variant thereof, adequate to produce antibody and/or T cell immune response to protect said individual from infection, particularly bacterial infection and most particularly *Staphylococcus aureus* infection. Also provided are methods whereby such immunological response slows bacterial replication. Yet another aspect of the invention relates to a method of inducing immunological response in an individual which comprises delivering to such individual a nucleic acid vector to direct expression of secA2, or a fragment or a variant thereof, for expressing secA2, or a fragment or a variant thereof in vivo in order to induce an immunological response, such as, to produce antibody and/or T cell immune response, including, for example, cytokine-producing T cells or cytotoxic T cells, to protect said individual from disease, whether that disease is already established within the individual or not. One way of administering the gene is by accelerating it into the desired cells as a coating on particles or otherwise.

Such nucleic acid vector may comprise DNA, RNA, a modified nucleic acid, or a DNA/RNA hybrid.

A further aspect of the invention relates to an immunological composition which, when introduced into an individual capable or having induced within it an immunological response, induces an immunological response in such individual to a secA2 or protein coded therefrom, wherein the composition comprises a recombinant secA2 or protein coded therefrom comprising DNA which codes for and expresses an antigen of said secA2 or protein coded therefrom. The immunological response may be used therapeutically or prophylactically and may take the form of antibody immunity or cellular immunity such as that arising from CTL or CD4+ T cells.

A secA2 polypeptide or a fragment thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as lipoprotein D from *Hemophilus influenzae*, Glutathione-S-transferase (GST) or beta-galactosidase, relatively large co-proteins which solubilize the protein and facilitate production and purification thereof. Moreover, the co-protein may act as an adjuvant in the sense of providing a generalized stimulation of the immune system. The co-protein may be attached to either the amino or carboxy terminus of the first protein.

Provided by this invention are compositions, particularly vaccine compositions, and methods comprising the polypeptides or polynucleotides of the invention and immunostimulatory DNA sequences, such as those described in Sato, Y. et al. Science 273: 352 (1996).

Also, provided by this invention are methods using the described polynucleotide or particular fragments thereof which have been shown to encode non-variable regions of bacterial cell surface proteins in DNA constructs used in such genetic immunization experiments in animal models of infection with *Staphylococcus aureus* will be particularly useful for identifying protein epitopes able to provoke a prophylactic or therapeutic immune response. It is believed that this approach will allow for the subsequent preparation of monoclonal antibodies of particular value from the requisite organ of the animal successfully resisting or clearing infection for the development of prophylactic agents or therapeutic treatments of bacterial infection, particularly *Staphylococcus aureus* infection, in mammals, particularly humans.

The polypeptide may be used as an antigen for vaccination of a host to produce specific antibodies which protect against invasion of bacteria, for example by blocking adherence of bacteria to damaged tissue. Examples of tissue damage include wounds in skin or connective tissue caused, e.g., by mechanical, chemical or thermal damage or by implantation of indwelling devices, or wounds in the mucous membranes, such as the mouth, mammary glands, urethra or vagina.

The invention also includes a vaccine formulation which comprises an immunogenic recombinant protein of the invention together with a suitable carrier. Since the protein may be broken down in the stomach, it is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostats and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

While the invention has been described with reference to certain secA2 protein, it is to be understood that this covers fragments of the naturally occurring protein and similar proteins with additions, deletions or substitutions which do not substantially affect the immunogenic properties of the recombinant protein.

Compositions, kits and administration

The invention also relates to compositions comprising the polynucleotide or the polypeptides discussed above or their agonists or antagonists. The polypeptides of the invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with one or more of the ingredients of the aforementioned compositions of the invention.

Polypeptides and other compounds of the invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent bacterial wound infections, especially *Staphylococcus aureus* wound infections.

Many orthopaedic surgeons consider that humans with prosthetic joints should be considered for antibiotic prophylaxis before dental treatment that could produce a bacteremia. Late deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

Alternatively, the composition of the invention may be used to bathe an indwelling device immediately before insertion. The active agent will preferably be present at a concentration of 1 $\mu$/ml to 10 mg/ml for bathing of wounds or indwelling devices.

A vaccine composition is conveniently in injectable form. Conventional adjuvants may be employed to enhance the immune response. A suitable unit dose for vaccination is 0.5–5 microgram/kg of antigen, and such dose is preferably administered 1–3 times and with an interval of 1–3 weeks. With the indicated dose range, no adverse toxicological effects will be observed with the compounds of the invention which would preclude their administration to suitable individuals.

Each reference disclosed herein is incorporated by reference herein in its entirety. Any patent application to which this application claims priority is also incorporated by reference herein in its entirety.

EXAMPLES

The examples below are carried out using standard techniques, which are well known and routine to those of skill in the art, except where otherwise described in detail. The examples are illustrative, but do not limit the invention.

Example 1
Strain Selection, Library Production and Sequencing

The polynucleotide having the DNA sequence given in SEQ ID NO:1 was obtained from a library of clones of chromosomal DNA of *Staphylococcus aureus* in *E. coli*. The sequencing data from two or more clones containing overlapping *Staphylococcus aureus* DNAs was used to construct the contiguous DNA sequence in SEQ ID NO:1. Libraries may be prepared by routine methods, for example: Methods 1 and 2 below.

Total cellular DNA is isolated from *Staphylococcus aureus* WCUH 29 according to standard procedures and size-fractionated by either of two methods.

Method 1

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and *E.coli* infected with the packaged library. The library is amplified by standard procedures.

Method 2

Total cellular DNA is partially hydrolyzed with a one or a combination of restriction enzymes appropriate to generate a series of fragments for cloning into library vectors (e.g., RsaI, PalI, AluI, Bshl235I), and such fragments are size-fractionated according to standard procedures. EcoRI linkers are ligated to the DNA and the fragments then ligated into the vector Lambda ZapII that have been cut with EcoRI, the library packaged by standard procedures, and *E.coli* infected with the packaged library. The library is amplified by standard procedures.

Example 2
secA2 Characterization

This assay involves a modification of the *E.coli* in vitro translocation assay which is well documented in the literature (11,12,13). Inside-out membrane vesicles from *S. aureus* are prepared as described by Schimz et al. (14). Purified SecA2 is added to urea washed membrane vesicles in the presence of Mg-ATP and test compound and the reaction started by the addition of a small volume of an appropriate preprotein substrate (for example, proOmpA (11,12,13) or preprolipase(14)) The inorganic phosphate released by ATP hydrolysis is then quantified by a colorimetric assay described by Lanzetta et al. (15). Thus inhibitors of SecA2 can be detected by a reduction in amount of inorganic phosphate produced relative to the control.

References

13. Cabelli, R. J. et al. (1988) Cell 55, 683–692.
14. Cunningham, K. et al. (1989) The EMBO Journal 8, 955–959.
15. Lill, R. et al. (1990) Cell 60, 271–280.
16. Schimz, K.-L. et al. (1995) FEBS Letters 362, 29–33.
17. Lanzetta, P. A. et al. (1979) Analytical Biochemistry 100, 95–97.

What is claimed is:

1. An isolated polynucleotide segment comprising a nucleic acid sequence that encodes a polypeptide comprising the amino acid sequence of SEQ ID NO:2, wherein the nucleic acid sequence is not genomic DNA.

2. An isolated polynucleotide segment comprising a nucleic acid sequence of SEQ ID NO:1, wherein the nucleic acid sequence is not genomic DNA.

3. A vector comprising the isolated polynucleotide segment of claim 1 or 2.

4. A host cell comprising the vector of claim 3.

5. A process for producing a polypeptide comprising the step of culturing the host cell of claim 4 under conditions sufficient for the production of the polypeptide.

6. An isolated polynucleotide segment comprising a nucleic acid sequence that is fully complementary to a reference polynucleotide that encodes a polypeptide comprising the amino acid sequence of SEQ ID NO:2, wherein the nucleic acid sequence is not genomic DNA.

7. An isolated polynucleotide segment comprising a nucleic acid sequence that is fully complementary to SEQ ID NO:1, wherein the nucleic acid sequence is not genomic DNA.

8. A vector comprising the isolated polynucleotide segment of claim 6 or 7.

9. A host cell comprising the vector of claim 8.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
    (A) LENGTH: 2388 base pairs
    (B) TYPE: nucleic acid
    (C) STRANDEDNESS: double
    (D) TOPOLOGY: linear (xi) SEQUENCE DESCRIPTION: SEQ ID NO:1:

```
ATGAAACATA AACTAGATGT TACGATAAAC GAATTAAGAC TAAAGTCGAT TAGAAAAATA    60

GTGAAACGCA TCAATACATG GAGCGATGAA GTTAAATCAT ATTCTGATGA TGCGTTAAAA   120

CAAAAGACAA TAGAATTTAA AGAACGTTTA GCATCAGGAG TTGATACACT AGATACATTG   180

TTACCTGAAG CTTATGCAGT GGCACGTGAA GCGAGCTGGA GAGTATTAGG TATGTATCCT   240

AAAGAAGTTC AGTTAATCGG AGCGATTGTA TTGCATGAAG GTAACATTGC GGAGATGCAA   300

ACAGGCGAAG GTAAAACATT AACGGCAACG ATGCCTTTAT ATTTAAATGC TCTTTCGGGA   360

AAAGGAACAT ATTTAATTAC AACGAATGAT TATTTAGCGA AGCGAGATTT TGAAGAGATG   420

CAACCATTAT ATGAATGGTT AGGTTTAACT GCTTCATTAG GTTTTGTTGA TATTGTGGAT   480

TATGAGTATC AAAAAGGGGA AAAACGTAAT ATATATGAAC ATGATATTAT ATACAACT    540

AATGGACGTC TCGGTTTTGA TTATTTAATT GATAATTTGG CTGATAGTGC GGAAGGGAAA   600

TTTTTACCAC AATTAAATTA CGGTATTATT GATGAAGTGG ATTCAATCAT TTTAGATGCT   660

GCTCAAACAC CATTAGTTAT TTCGGGTGCA CCAAGATTAC AATCAAATCT ATTTCATATT   720

GTGAAAGAGT TTGTAGATAC ATTGATTGAA GACGTGCATT TTAAAATGAA GAAGACCAAA   780

AAAGAAATAT GGCTGTTAAA TCAAGGTATT GAAGCGGCAC AATCATACTT TAATGTTGAA   840

GATTTATATA GCGAACAAGC GATGGTCCTA GTGCGTAATA TTAATTTAGC ACTGCGCGCA   900

CAATATTTGT TTGAATCTAA TGTCGATTAC TTTGTATATA ATGGTGATAT TGTTTTAATT   960

GACCGTATTA CAGGTCGTAT GTTACCGGGA ACTAAGTTGC AAGCTGGACT TCACCAAGCT  1020

ATTGAAGCGA AGAAGGTAT GGAGGTTTCA ACAGATAAAA GTGTTATGGC AACAATTACC  1080

TTCCAGAATT TATTTAAACT TTTTGAATCA TTTTTCAGGTA TGACAGCTAC AGGAAAATTA  1140

GGCGAATCAG AGTTCTTTGA TTTGTATTCA AAAATAGTCG TACAAGCACC AACTGATAAA  1200

GCGATTCAAC GTATCGATGA ACCAGATAAA GTGTTTCGTT CAGTTGATGA GAAAAACATC  1260

GCGATGATTC ATGATATAGT TGAACTTCAT GAAACGGGGC GACCGGTTTT ACTCATAACG  1320

AGAACTGCTG AAGCGGCTGA ATACTTTTCC GAAGTATTAT TCCAAATGGA TATTCCTAAT  1380

AATTTACTCA TTGCGCAAAA TGTTGCAAAA GAAGCGCAGA TGATAGCTGA AGCAGGGCAA  1440

ATTGGTTCCA TGACTGTTGC GACTAGTATG GCAGGTCGAG GCACAGATAT TAAACTTGGT  1500

GAAGGTGTCG AAGCATTAGG TGGATTAGCT GTTATTATTC ATGAACATAT GGAAAATAGC  1560

CGTGTAGACA GGCAATTACG TGGTCGTTCT GGTAGACAAG GGGATCCGGG ATCATCTTGT  1620

ATATATATTT CACTAGATGA TTATTTAGTT AAGCGATGGA GCGATAGTAA TTTAGCGGAA  1680

AATAATCAAT TATATTCATT AGATGCACAA CGATTATCGC AAAGTAATTT GTTTAATCGC  1740

AAAGTTAAGC AAATTGTAGT TAAAGCGCAG CGTATCTCGG AAGAACAAGG GGTTAAAGCT  1800

CGTGAAATGG CTAATGAATT TGAAAAAAGC ATTAGTATAC AGCGAGATCT TGTATACGAG  1860

GAACGCAATC GAGTTTTAGA AATAGATGAT GCTGAGAATC GAGATTTTAA AGCGTTAGCT  1920

AAAGATGTAT TTGAAATGTT TGTAAATGAG GAAAAGGTGC TAACAAAATC GCGTGTTGTC  1980

GAGTATATTT ATCAAAATTT AAGTTTCCAA TTTAATAAAG ATGTGGCTTG TGTTAATTTT  2040

AAAGATAAGC AAGCAGTAGT GACATTTTTA TTAGAGCAAT TTGAAAAGCA ATTAGCTTTG  2100
```

```
AATCGTAAAA ACATGCAAAG TGCATATTAT TATAATATTT TCGTTCAAAA AGTCTTTTTG    2160

AAAGCAATTG ATTCATGTTG GTTAGAACAA GTCGACTATT TACAACAATT AAAAGCAAGC    2220

GTTAATCAAC GACAAAATGG GCAACGTAAC GCTATTTTTG AATACCATAG AGTTGCATTA    2280

GATTCATTTG AAGTTATGAC ACGAAATATC AAAAAAAGAA TGGTGAAAAA TATTTGTCAA    2340

AGCATGATTA CATTTGATAA AGAGGGTATG CCAGTTATAC ATTTTCCA                2388
```

(2) INFORMATION FOR SEQ ID NO:2:

(i) SEQUENCE CHARACTERISTICS:
        (A) LENGTH: 796 amino acids
        (B) TYPE: amino acid
        (C) STRANDEDNESS: single
        (D) TOPOLOGY: linear (xi) SEQUENCE DESCRIPTION: SEQ ID NO:2:

```
Met Lys His Lys Leu Asp Val Thr Ile Asn Glu Leu Arg Leu Lys Ser
 1               5                  10                  15

Ile Arg Lys Ile Val Lys Arg Ile Asn Thr Trp Ser Asp Glu Val Lys
            20                  25                  30

Ser Tyr Ser Asp Asp Ala Leu Lys Gln Lys Thr Ile Glu Phe Lys Glu
        35                  40                  45

Arg Leu Ala Ser Gly Val Asp Thr Leu Asp Thr Leu Pro Glu Ala
    50                  55                  60

Tyr Ala Val Ala Arg Glu Ala Ser Trp Arg Val Leu Gly Met Tyr Pro
65                  70                  75                  80

Lys Glu Val Gln Leu Ile Gly Ala Ile Val Leu His Glu Gly Asn Ile
                85                  90                  95

Ala Glu Met Gln Thr Gly Glu Gly Lys Thr Leu Thr Ala Thr Met Pro
            100                 105                 110

Leu Tyr Leu Asn Ala Leu Ser Gly Lys Gly Thr Tyr Leu Ile Thr Thr
        115                 120                 125

Asn Asp Tyr Leu Ala Lys Arg Asp Phe Glu Glu Met Gln Pro Leu Tyr
    130                 135                 140

Glu Trp Leu Gly Leu Thr Ala Ser Leu Gly Phe Val Asp Ile Val Asp
145                 150                 155                 160

Tyr Glu Tyr Gln Lys Gly Glu Lys Arg Asn Ile Tyr Glu His Asp Ile
                165                 170                 175

Ile Tyr Thr Thr Asn Gly Arg Leu Gly Phe Asp Tyr Leu Ile Asp Asn
            180                 185                 190

Leu Ala Asp Ser Ala Glu Gly Lys Phe Leu Pro Gln Leu Asn Tyr Gly
        195                 200                 205

Ile Ile Asp Glu Val Asp Ser Ile Ile Leu Asp Ala Ala Gln Thr Pro
    210                 215                 220

Leu Val Ile Ser Gly Ala Pro Arg Leu Gln Ser Asn Leu Phe His Ile
225                 230                 235                 240

Val Lys Glu Phe Val Asp Thr Leu Ile Glu Asp Val His Phe Lys Met
                245                 250                 255

Lys Lys Thr Lys Lys Glu Ile Trp Leu Leu Asn Gln Gly Ile Glu Ala
            260                 265                 270

Ala Gln Ser Tyr Phe Asn Val Asp Leu Tyr Ser Glu Gln Ala Met
        275                 280                 285

Val Leu Val Arg Asn Ile Asn Leu Ala Leu Arg Ala Gln Tyr Leu Phe
    290                 295                 300

Glu Ser Asn Val Asp Tyr Phe Val Tyr Asn Gly Asp Ile Val Leu Ile
```

-continued

```
305                 310                 315                 320

Asp Arg Ile Thr Gly Arg Met Leu Pro Gly Thr Lys Leu Gln Ala Gly
                325                 330                 335

Leu His Gln Ala Ile Glu Ala Lys Glu Gly Met Glu Val Ser Thr Asp
                340                 345                 350

Lys Ser Val Met Ala Thr Ile Thr Phe Gln Asn Leu Phe Lys Leu Phe
                355                 360                 365

Glu Ser Phe Ser Gly Met Thr Ala Thr Gly Lys Leu Gly Glu Ser Glu
                370                 375                 380

Phe Phe Asp Leu Tyr Ser Lys Ile Val Val Gln Ala Pro Thr Asp Lys
385                 390                 395                 400

Ala Ile Gln Arg Ile Asp Glu Pro Asp Lys Val Phe Arg Ser Val Asp
                405                 410                 415

Glu Lys Asn Ile Ala Met Ile His Asp Ile Val Glu Leu His Glu Thr
                420                 425                 430

Gly Arg Pro Val Leu Leu Ile Thr Arg Thr Ala Glu Ala Ala Glu Tyr
                435                 440                 445

Phe Ser Glu Val Leu Phe Gln Met Asp Ile Pro Asn Asn Leu Leu Ile
                450                 455                 460

Ala Gln Asn Val Ala Lys Glu Ala Gln Met Ile Ala Glu Ala Gly Gln
465                 470                 475                 480

Ile Gly Ser Met Thr Val Ala Thr Ser Met Ala Gly Arg Gly Thr Asp
                485                 490                 495

Ile Lys Leu Gly Glu Gly Val Glu Ala Leu Gly Gly Leu Ala Val Ile
                500                 505                 510

Ile His Glu His Met Glu Asn Ser Arg Val Asp Arg Gln Leu Arg Gly
                515                 520                 525

Arg Ser Gly Arg Gln Gly Asp Pro Gly Ser Ser Cys Ile Tyr Ile Ser
530                 535                 540

Leu Asp Asp Tyr Leu Val Lys Arg Trp Ser Asp Ser Asn Leu Ala Glu
545                 550                 555                 560

Asn Asn Gln Leu Tyr Ser Leu Asp Ala Gln Arg Leu Ser Gln Ser Asn
                565                 570                 575

Leu Phe Asn Arg Lys Val Lys Gln Ile Val Val Lys Ala Gln Arg Ile
                580                 585                 590

Ser Glu Glu Gln Gly Val Lys Ala Arg Glu Met Ala Asn Glu Phe Glu
                595                 600                 605

Lys Ser Ile Ser Ile Gln Arg Asp Leu Val Tyr Glu Glu Arg Asn Arg
                610                 615                 620

Val Leu Glu Ile Asp Asp Ala Glu Asn Arg Asp Phe Lys Ala Leu Ala
625                 630                 635                 640

Lys Asp Val Phe Glu Met Phe Val Asn Glu Glu Lys Val Leu Thr Lys
                645                 650                 655

Ser Arg Val Val Glu Tyr Ile Tyr Gln Asn Leu Ser Phe Gln Phe Asn
                660                 665                 670

Lys Asp Val Ala Cys Val Asn Phe Lys Asp Lys Gln Ala Val Val Thr
                675                 680                 685

Phe Leu Leu Glu Gln Phe Glu Lys Gln Leu Ala Leu Asn Arg Lys Asn
                690                 695                 700

Met Gln Ser Ala Tyr Tyr Tyr Asn Ile Phe Val Gln Lys Val Phe Leu
705                 710                 715                 720

Lys Ala Ile Asp Ser Cys Trp Leu Glu Gln Val Asp Tyr Leu Gln Gln
                725                 730                 735
```

```
Leu Lys Ala Ser Val Asn Gln Arg Gln Asn Gly Gln Arg Asn Ala Ile
            740                 745                 750

Phe Glu Tyr His Arg Val Ala Leu Asp Ser Phe Glu Val Met Thr Arg
            755                 760                 765

Asn Ile Lys Lys Arg Met Val Lys Asn Ile Cys Gln Ser Met Ile Thr
            770                 775                 780

Phe Asp Lys Glu Gly Met Pro Val Ile His Phe Pro
785                 790                 795

(2) INFORMATION FOR SEQ ID NO:3:

(i) SEQUENCE CHARACTERISTICS:
         (A) LENGTH: 1496 base pairs
         (B) TYPE: nucleic acid
         (C) STRANDEDNESS: double
         (D) TOPOLOGY: linear (xi) SEQUENCE DESCRIPTION: SEQ ID NO:3:

GTTAATCAAG TATCGAAGCG GAACAATCAT ACTTTAATGT TGAAGATTTA TATNGCGAAC      60

AAGCGATGGT CCTAGTGCGT AATATTAATT TAGCACTGCG CGCACAATAT TTGTTNGNAT     120

CTNATGTCGA TTACTTTGTA TATNNTGGTG ATATTGTTTT AACTGACCNC ATTACAGGTC     180

GTNTGTTACC GGNAACTAAG TTGCAAGCTG GACTTCACCA NGCTATTGAA GCGAAAGAAG     240

GTATGGAGGT TTCAACAGAT AAAAGTGTTA TGCCAACCAA TTACCCTTCC AGAATTTATT     300

TAAACTTTTT GAATCAATTT TCAGGTATGA CAAGCTACAG GAAAATTAGG CGAATCAGAG     360

TTCTTTGATT TGTATTCANA AATAGTCGTA CAAGCACCCA ACTGATAAAG CGATTCAACG     420

TATCGATGAA CCAGATAAAG TGTTTCGTTC AGTTGATGAG AAAAACATCG CGATGATTCA     480

TTGATATAGT TGAACTTCAT GANNCGGGGC CGACCGGTTT TACCTCATAA CCGAGNACTG     540

CTGAAGCGGC TTGAATACTT TTCNGAAGTA TTATTCCAAA TGGATATTCC TAATAATTTA     600

CTCATTGCGC AAAATGTTCC AAAAGAAGCG CAGATGATAG CTGAAGCAGG CCAAATTGGT     660

TCCATGACTG TTGCGACTAG TATGGCAGGT CGAGGCACAG ATATTAAACT TGGTGAAGGT     720

GTCGAAGCAT TAGCTGGATT AGCTGTTATT ATTCATGAAC ATATGGAAAA TAGCCGTGTA     780

GACAGGCAAT TACGTGGTCG TTCTGGTAGA CAAGGGGATC CGGGATCATC TTGTATATAT     840

ATTTCACTAG ATGATTATTT AGNTAAGCGA TGGAGCGATA GTAATTTAGC GGAAAATAAT     900

CAATTATATT CANTAGATGC ACAACGATTA TCGCAAAGTA ATTTGTTTAA TCGNAAAGTT     960

AAGCAAATTG TAGTTAAAGC GCAGCGTATC TCGGAAAGAA CAAGGGGTTA AGCTCGGTG    1020

AAATGGCTTA ATTGAATTTG NNAAAAAGCA TNAGTATTCA GCGAAGATCT TNGTATTTAC    1080

GANGGAACGC AAATCCGAGT TTTTAGAAAT TAGATTGATG CTGAGAATCC NAGATTTTTA    1140

ANGCGGTTAG CTTAAAGATT GTATTTGAAA TNGTTTGGGG NAATGANGGA AANGGTGCTA    1200

ACAAAATCGC GNGTTGGGCG AGTATATTTT ATCAAAAATT TAAGTTNCCA ATTTAATAAA    1260

GATGTGGCTT GTGTTAATTT TAAAGATAAG CAAGCAGNAG TGACATTTTT ATTAGAGCAA    1320

TTTGAAAAGC AATTAGCTTT GGANTCCGTA AAAACATGCA ANGNGCATAT TATTATAATA    1380

TTNCCGGCCA AAANGTCTTT NGGGAAAGCA ATTGATNCAA GTTGGGGTTA GGAACAAGTC    1440

GGCTTTTNAC AACAANTTAA NAGCAAGCGN TAATCAAACG ACAAAANTGG CAACCT       1496

(2) INFORMATION FOR SEQ ID NO:4:

(i) SEQUENCE CHARACTERISTICS:
         (A) LENGTH: 143 amino acids
```

```
        (B) TYPE: amino acid
        (C) STRANDEDNESS: single
        (D) TOPOLOGY: linear (xi) SEQUENCE DESCRIPTION: SEQ ID NO:4:

Met Asp Ile Pro Asn Asn Leu Leu Ile Ala Gln Asn Val Pro Lys Glu
 1               5                  10                  15

Ala Gln Met Ile Ala Glu Ala Gly Gln Ile Gly Ser Met Thr Val Ala
            20                  25                  30

Thr Ser Met Ala Gly Arg Gly Thr Asp Ile Lys Leu Gly Glu Gly Val
            35                  40                  45

Glu Ala Leu Ala Gly Leu Ala Val Ile Ile His Glu His Met Glu Asn
        50                  55                  60

Ser Arg Val Asp Arg Gln Leu Arg Gly Arg Ser Gly Arg Gln Gly Asp
 65                  70                  75                  80

Pro Gly Ser Ser Cys Ile Tyr Ile Ser Leu Asp Asp Tyr Leu Xaa Lys
                85                  90                  95

Arg Trp Ser Asp Ser Asn Leu Ala Glu Asn Asn Gln Leu Tyr Ser Xaa
                100                 105                 110

Asp Ala Gln Arg Leu Ser Gln Ser Asn Leu Phe Asn Arg Lys Val Lys
            115                 120                 125

Gln Ile Val Val Lys Ala Gln Arg Ile Ser Glu Arg Thr Arg Gly
        130                 135                 140

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:5:

ATGAAACATA AACTAGATGT TACG                                          24

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:6:

TGGAAAATGT ATAACTGGCA TACC                                          24
```